(12) United States Patent
Dick et al.

(10) Patent No.: US 7,066,928 B2
(45) Date of Patent: Jun. 27, 2006

(54) METHOD AND DEVICE FOR REPRESENTING AN OPERATIVE FIELD DURING LASER OPERATIONS

(75) Inventors: Manfred Dick, Gefell (DE); Juergen Kuehnert, Jena (DE); Holger Maeusezahl, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 10/481,988

(22) PCT Filed: Jun. 26, 2002

(86) PCT No.: PCT/EP02/07073

§ 371 (c)(1),
(2), (4) Date: Dec. 24, 2003

(87) PCT Pub. No.: WO03/002047

PCT Pub. Date: Jan. 9, 2003

(65) Prior Publication Data

US 2004/0176753 A1   Sep. 9, 2004

(30) Foreign Application Priority Data

Jun. 26, 2001   (DE) .................... 101 30 278

(51) Int. Cl.
*A61F 9/008*   (2006.01)

(52) U.S. Cl. .......................... 606/5; 606/4
(58) Field of Classification Search ............ 606/5
See application file for complete search history.

(56) References Cited

U.S. PATENT DOCUMENTS

| | | | | |
|---|---|---|---|---|
| 4,307,944 A | * | 12/1981 | Schirmer | 351/214 |
| 4,715,703 A | * | 12/1987 | Cornsweet et al. | 351/214 |
| 5,029,220 A | * | 7/1991 | Juday | 382/128 |
| 5,049,147 A | * | 9/1991 | Danon | 606/10 |
| 5,098,426 A | | 3/1992 | Sklar et al. | |
| 5,350,374 A | * | 9/1994 | Smith | 606/5 |
| 5,715,836 A | | 2/1998 | Kliegis et al. | 128/898 |
| 6,099,522 A | | 8/2000 | Knopp et al. | |
| 6,176,582 B1 | | 1/2001 | Grasnick | 353/7 |
| 6,210,169 B1 | * | 4/2001 | Yavitz | 434/271 |
| 6,290,695 B1 | | 9/2001 | Kuhnert et al. | 606/5 |
| 6,302,876 B1 | * | 10/2001 | Shimmick et al. | 606/5 |
| 6,394,999 B1 | * | 5/2002 | Williams et al. | 606/5 |
| 6,454,761 B1 | * | 9/2002 | Freedman | 606/5 |
| 6,467,907 B1 | * | 10/2002 | Fujieda et al. | 351/212 |
| 6,478,792 B1 | * | 11/2002 | Hansel | 606/5 |
| 6,500,171 B1 | * | 12/2002 | Williams et al. | 606/5 |
| 6,585,723 B1 | * | 7/2003 | Sumiya | 606/5 |
| 6,605,081 B1 | * | 8/2003 | Shimmick et al. | 606/10 |
| 6,726,680 B1 | * | 4/2004 | Knopp et al. | 606/12 |
| 2004/0020983 A1 | | 2/2004 | Feige et al. | 235/382 |

FOREIGN PATENT DOCUMENTS

| | | |
|---|---|---|
| DE | 43 04 571 A1 | 8/1994 |
| DE | 197 27 573 C1 | 5/1998 |
| DE | 198 25 950 C1 | 2/2000 |
| DE | 100 52 201 A1 | 5/2002 |

\* cited by examiner

*Primary Examiner*—Michael F Peffley
*Assistant Examiner*—Henry M Johnson, III
(74) *Attorney, Agent, or Firm*—Davidson, Davidson & Kappel, LLC

(57) ABSTRACT

The invention relates to a device for the three-dimensional representing of an operative field, especially of an eye, during laser operations. The inventive device comprises a three-dimensional recording system, an image processing system and a three-dimensional display unit.

15 Claims, 3 Drawing Sheets

METHOD AND DEVICE FOR REPRESENTING AN OPERATIVE FIELD DURING LASER OPERATIONS

BACKGROUND

The present invention relates to a method and a device for the representation of an operation area during laser operations.

In ophthalmology, it is known in the case of poor eyesight to shape the cornea by the ablation of tissue. As methods, the so-called PRK (photorefractive keratectomy) and LASIK (laser-assisted in situ keratomileusis) methods have established themselves, in which initially a small flap of epithelium, Bowman membrane and stroma is cut and unfolded and then the PRK is carried out in the stroma bed.

Lasers of suitable wavelength are used for ablation. The excimer laser with a wavelength of 193 nm is particularly suitable for this purpose. However, other lasers such as Er:YAG solid-state lasers are also already used for this.

The data for the extent of the defective vision are established by sight tests, by means of refractometers and recently also by the evaluation of measurements of the wavefront. Other methods and devices are also known, which can be used to calculate firing coordinates for the actual operative procedure from these measurement values.

A laser operation is monitored by the surgeon or doctor usually by observing the operation area by means of a microscope. The doctor thus obtains a spatial impression of the operation area. However, the view through the microscope allows only one person a spatial impression.

Representation on a monitor etc. by means of a camera is also known. However, in this case the spatial impression of the operation area is lost. In the case of an operation using a slit scanner, the progress of the operation and the sequence of the ablation steps can be very well perceived and monitored by the doctor. The doctor can thus detect abnormalities in the ablation process early and counteract these, for example stop the operation, etc.

With today's modern spot scanners, the ablation process is no longer easy to understand due to various factors. Firstly, the firing frequency of the lasers is increasing all the time and lies well above the perceptive capability of the surgeon. The ablation process is also patient-dependent and the steering and placement of the spot in the ablation area is subject to complex algorithms which attempt to solve the most varied tasks and problems of the ablation process (thermal load, smoke). An ablation algorithm for example breaks down the necessary firings for a complete correction into many small individual corrections, with the aim that the operation can be aborted at any time and it can be guaranteed that an optically satisfactory result is achieved (cf. the valuable contribution to the state of the art in the patent specification DE 197 27 573). Therefore, in the case of more modern spot scanners, it is no longer possible for a surgeon to monitor the complex ablation process—by checking the correct positioning of the laser beam on the area to be operated on—by "looking through the microscope".

The field of vision is also seriously limited when "looking through the microscope" because of the design. In order to use operation equipment, to ascertain status information or progress information for equipment, the doctor must stop looking through the operation microscope and therefore take his eyes off the operation area.

When representing the operation area for several observers (teaching purposes, monitoring etc.), the operation area can be represented by means of a camera and a monitor. Because of the principle involved, however, the spatial impression is lost in this case. However, this is of decisive importance during such microsurgical procedures.

The ablation processes in PRK using a spot scanner are so complex that the doctor is scarcely in a position to tell whether the operation is progressing correctly or to detect, early, problems which arise, so as to act to correct them. In order to control equipment etc., the doctor must take his eyes off the operation area, in order to use the equipment or to record status information.

SUMMARY OF THE INVENTION

An object of the invention is to make available devices and methods which allow the doctor to be able to clearly monitor the progress of the operation and thus to consciously control the operation.

The present invention provides a device for the three-dimensional representation of an operation area, in particular an eye, during laser operations, comprising a spatial recording system (10), an image-processing system (15) and a spatial display unit (20). This device makes it possible to three-dimensionally represent the operation area and to clearly monitor the progress of the operation, even when not looking through the microscope. In particular, in this way several observers can observe the operation area simultaneously, without losing the three-dimensional impression.

The spatial recording system is preferably a camera system, with which image information or data of an object can be obtained typically from several observation angles. These data then allow the reconstruction of a three-dimensional representation of this object, i.e. the operation area.

The image-processing system evaluates the obtained data and processes them so that they are suitable for the following spatial display unit for the representation of a three-dimensional or spatial image. The image-processing system can be a chip, a computer, software or a microprocessor.

The spatial display unit is preferably a 3-D display, a hologram or a three-dimensional representation unit generated by laser. Particularly preferably, it is an arrangement for three-dimensional representation according to DE 198 25 950. The spatial extent of the starting position, i.e. the position before the operative procedure, and also the spatial extent of the position after an operation can be advantageously represented by means of such a display.

In a preferred embodiment of the present invention, the device according to the invention also comprises a control module (30); at least one item of medical equipment (40) and a bus system which connects the spatial display unit (20) and the control module (30), so that data and information can be displayed on the display unit (20). It is hereby possible that additional information relating to the operation or the operation laser etc. can be displayed by the three-dimensional or spatial representation of the operation area which is to be observed. The surgeon and other observers can thus record valuable additional information without having to take their eyes off the spatially represented operation area.

The control module is preferably a computer, a calculator, a microcontroller.

The item of medical equipment preferably comprises an operation laser for refractive surgery. In addition, further devices such as eye trackers, online topography sensors, online wavefront sensors, illumination units and also eye identification systems (including rotation control and identification according to the application DE 10052201) can be used. This equipment sends data regarding its own status via the bus system to the control unit and also receives instructions from the control device via the bus system. Particularly preferably, the algorithm for the processing of the operation program and the data of the planned operation are also on the control unit or are fed into this or made available to this.

Data and information are particularly preferably data relating to the operation area, preferably a laser for refractive corneal surgery (such as firing rate, energy, pulse shape, etc.) or data regarding the operation (such as patient data, temperature of the tissue or operation area, operation time already elapsed, remaining time of the operation, operation laser settings, etc.) or status information (limits of the area of the eye tracker, limits of the operating range of the laser, progress of the operation, energy status, etc.).

In another preferred embodiment of the present invention, the device according to the invention also comprises a touch-sensitive display overlay. It is thereby possible for the surgeon to input control commands or equipment control functions via the touch-sensitive display overlay. These can be passed on to the control unit and from there be used to control the medical equipment.

In another preferred embodiment of the present invention, image data relating to the operation area, additional data and information and also control panels can be represented on the display unit (20). This representation of all relevant and interesting data for the operation makes it possible for the surgeon to keep his eye on all parameters and circumstances of the operation, without having to take his eye off the spatially represented operation area. These various data can be represented as a PIP (picture in a picture) or overlaid. The images and data can also be displayed in a multi-window technique.

In addition, it is possible to display several different views of the operation area simultaneously. These can be different observation angles, different perspectives, clips or magnification scales. It is also possible to represent images of different time domains next to each other, which is preferable in particular if the chronology of an operation is to be displayed. This is particularly interesting for teaching events in which the data and the course of previous operations is to be presented, without foregoing the spatial impression.

In particular panels and symbols, which can be activated by touching the touch-sensitive display overlay, are provided as control panels. These are preferably symbols for controlling a magnification of the image, in particular for infinitely variable magnification (digital zoom). Camera guiding symbols for selecting the perspective and the observation angle are also preferably provided, and symbols for selecting from the individual windows, etc.

A device is quite particularly preferred in which reference data of an ideal operation area after the operation, in particular of an ideal cornea shape, can be spatially represented on the spatial display unit (20) via an image of the current operation area, in particular of the current cornea. It is thereby possible to represent the data of the ideal cornea via the image of the current, curved cornea and thereby to illustrate the difference. During the operation, the manner in which the cornea operated on ever more closely resembles the ideal shape represented, and is finally made congruent with it, can be monitored live. Additionally, current deviations of the cornea that are established online can be compared with the initial correction values presently during the operation on the basis of a wavefront analysis and thus an even more precise correction can be illustrated during the actual course of the operation.

The starting position and desired final position can thus be represented such that the layer thickness to be ablated within the framework of the operative procedure (ablation volume) can be seen.

The device according to the invention also preferably has a simulation unit which, upon every single laser firing, realizes on the display an ablation which, in terms of location and volume ablation, precisely simulates the ablation that takes place during the ablation on the cornea. The device according to the invention is designed such that, during an operation, upon each laser firing on the display, a volume unit that is sufficient for the volume ablation on the eye is removed from the display. With the device according to the invention, the course of the ablation of the cornea can therefore be monitored by the surgeon.

In a preferred version, for every single firing, the coordinates for the volume removal are measured directly from the scanner on the display. In this way, the ablation takes place on the display at precisely the point which corresponds to the respective position of the scanners at this point. Should the scanners not assume the precise position, an ablation with correspondingly modified coordinates also takes place on the display. A greatly improved online control of the course of the operation by the surgeon is therefore possible by means of the device according to the invention. At the end of the operation, he can also record in a simple manner the final position that has been realized.

Should the realized final position not wholly correspond to the desired correction, the surgeon can decide whether he will immediately carry out a post-correction. Further coordinates for the ablation can thus be calculated from the realized final position and from the originally desired position, so that a post-correction can take place immediately afterwards.

Coordinates for a post-correction are preferably established automatically, so that the post-correction can be carried out immediately after the original program. This correction is also monitored on the display according to the idea of the invention. An online topography of the cornea surface can thus be represented on the spatial display unit.

The simulation unit is preferably also connected to the unit for controlling the laser energy. Should the laser energy differ from the proposed value, the simulated volume ablation can also be modified accordingly.

Furthermore, the simulation unit (monitoring unit) can be connected to an online wavefront sensor. The current wavefront of the eye is spatially represented. Through the spatial representation of the present wavefront of the eye during the operation, the surgeon can directly monitor the progress and success of the operation on the patient. Due to the invention, a wavefront which has been modified and differs from the ideal wavefront can also be displayed directly. This can arise due to unforeseeable factors during the operation. The spatial representation therefore makes it possible for the surgeon to make a sound decision to decide in favour of a further correction under other parameters (in order to also lead the new wavefront aberrations to an ideal wavefront) or to end the operation.

The present invention also provides a method for the three-dimensional representation of an operation area (1), in particular an eye, during laser operations, comprising the steps: recording of the operation area (1) by means of a spatial recording system (10), transfer of the information obtained from the preceding step to an image-processing system (15), processing of the information in the image-processing system (15) and representation of this processed information on a spatial display unit (20).

The method according to the invention preferably also comprises the step: representation of additional data on the spatial display unit (20). These data can, as stated above, be data and information concerning the patient, the progress of the operation or the medical equipment, in particular the operation laser.

Particularly preferably, the method according to the invention also comprises the steps: registration of control commands, in particular by touching a touch-sensitive display (25), steering medical equipment (40) in accordance with the registered control commands. These control commands can, as stated above, be camera-position and clip-selection commands and also control commands which directly relate to the operation laser (emergency stop, repetition of special sequences, re-calculation, etc.).

The device according to the invention and also the method according to the invention can be used in particular in the field of ophthalmology. For example, the material processing in the case of contact lenses or intraocular lenses (IOLs) can be monitored with the device according to the invention or the method according to the invention. As a rule, the processing does not take place on or in the eye. The observation of the processing procedure during series production of contact lenses or intraocular lenses is also conceivable. The control of the final position of the respective lenses is conceivable in particular here as an area of use of the device according to the invention and the method according to the invention.

It is also possible for the patient himself to monitor the production of a lens, for example an intraocular lens or a contact lens. In this way, he can form an impression beforehand of the chances of success. Monitoring the processing procedure of the individual lenses gives the patient confidence for the ensuing operation. The processed lens is preferably reflected in an intermediate image plane of an optical system.

A further possible use of the device according to the invention and the method according to the invention is the monitoring of the material processing on a contact lens located on the eye. Here, the entire eye/contact lens system can be measured together. The processing takes place only on the contact lens. The eye itself is not operated on.

The device according to the invention and the method according to the invention can also be used for non-medical applications. In principle, it is possible to use them in any type of processing of a surface by means of a laser.

BRIEF DESCRIPTION OF THE DRAWINGS

The invention will be explained further in the following with reference to drawings. Further advantageous features are described here. There are shown in.

DETAILED DESCRIPTION

Figure 1:
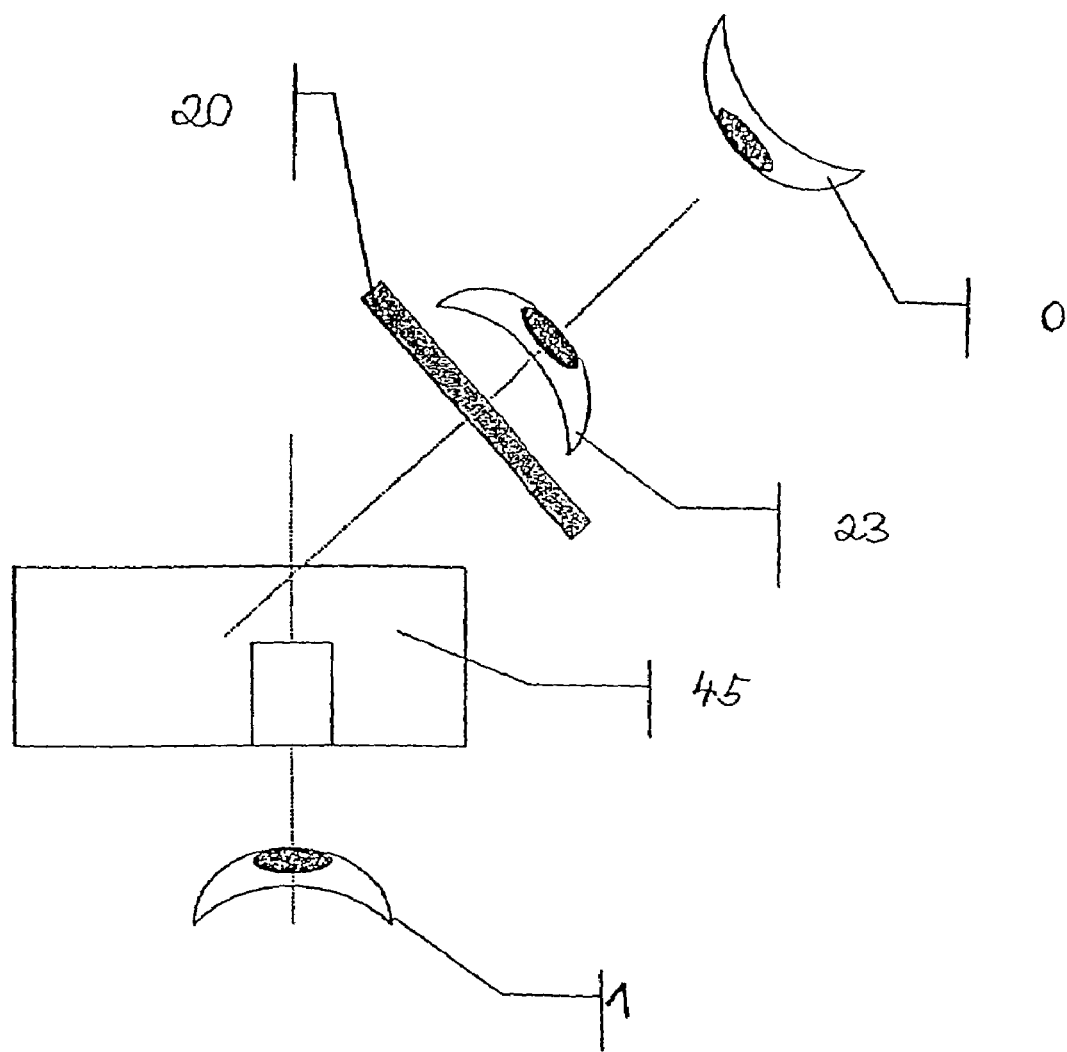
FIG. 1: a schematic representation of a device according to the invention.

FIG. 1 shows a schematic representation of a device according to the invention. A surgeon 0 observes a spatial image 23 of a patient's eye which is represented by a display for spatial representation 20. The eye of the patient 1 is then operated on by means of a laser 45.

Figure 2:
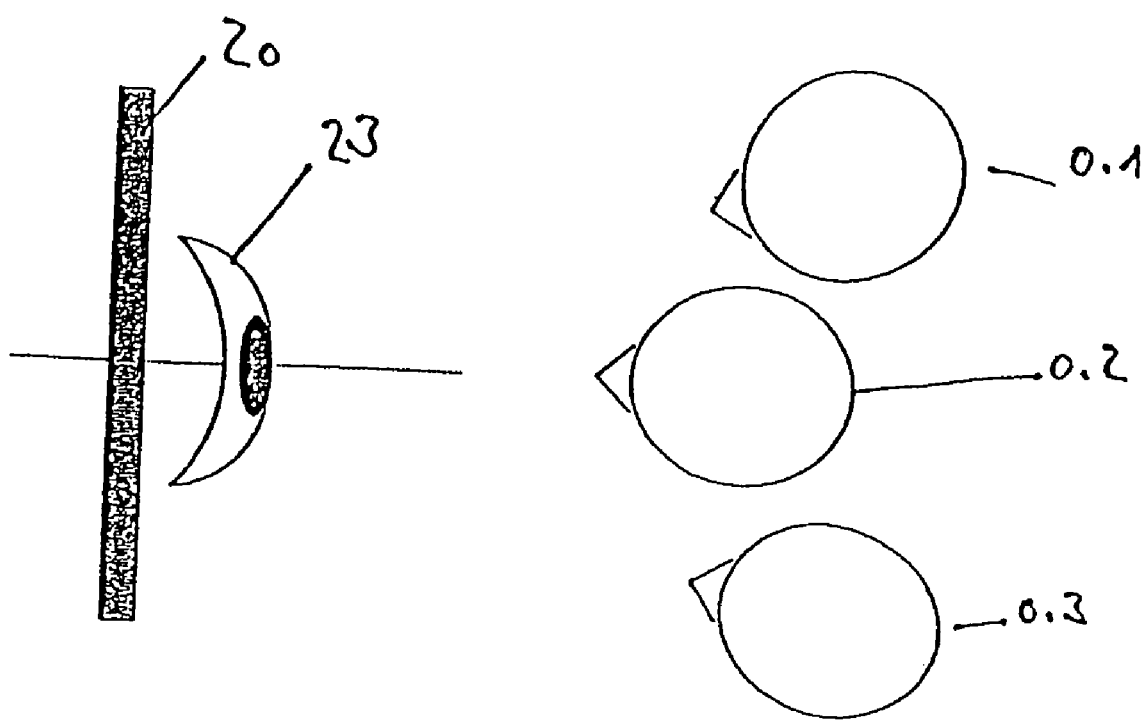
FIG. 2: a schematic representation of a device according to the invention for observation for more than one person.

FIG. 2 shows a schematic representation of a device according to the invention for observation for more than one person. Several observers 0.1, 0.2 and 0.3 simultaneously observe, by means of only one spatial display unit 20, the spatial image of the eye 23 to be treated.

Figure 3:
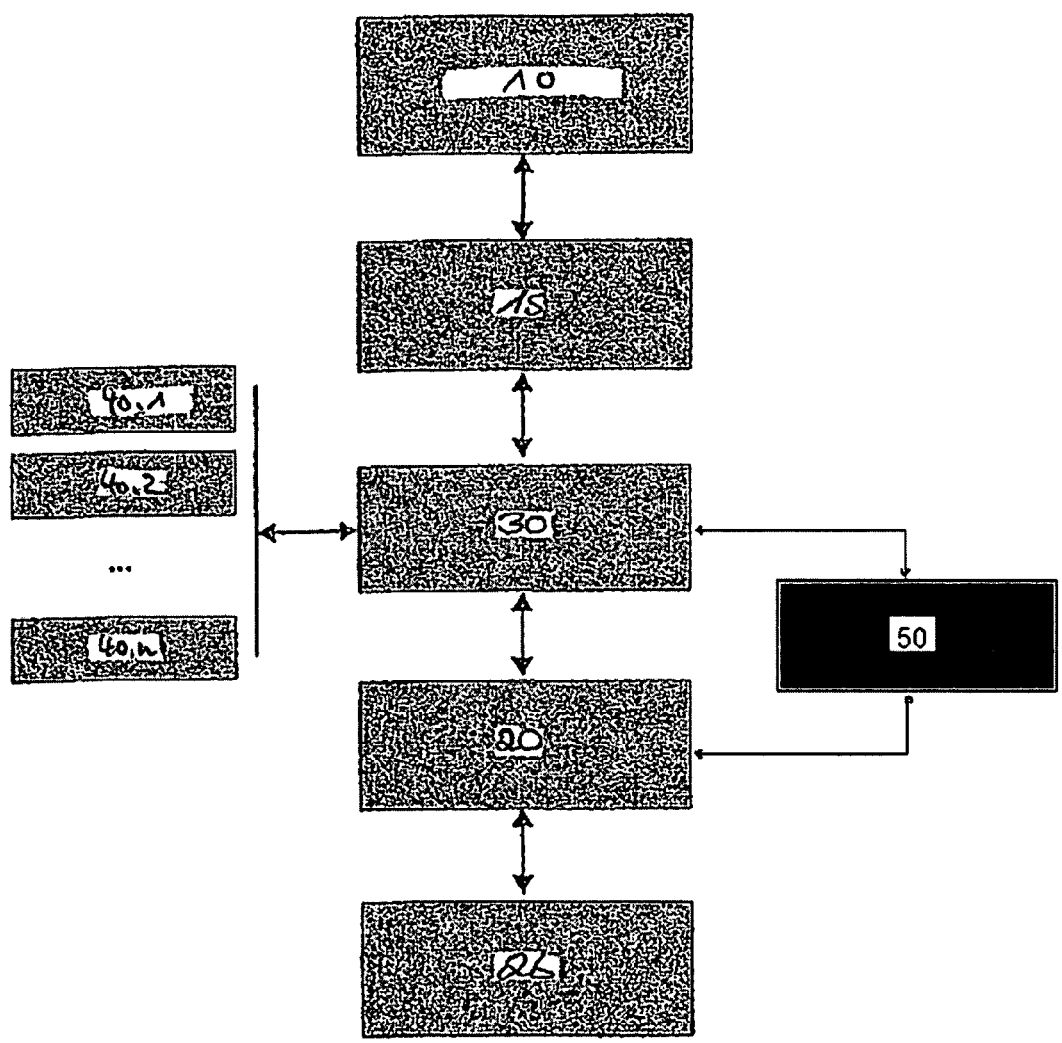
FIG. 3: a basic representation of the components of an embodiment of a device according to the present invention.

FIG. 3 shows a basic representation of the components of an embodiment of a device according to the present invention. A spatial recording system 10 is connected to an image-processing system 15. This is connected to a control module 30. The control module 30 connects medical equipment 40.1 to 40.n to the spatial display unit 20. A simulation unit 50 is connected to the control unit 30 and spatial displace unit 20. A touch-sensitive display overlay 25 is connected to the spatial display unit 20.

This structure according to the invention makes it possible to record three-dimensionally an operation area by the spatial recording system 10, to process these data via an image-processing system 15 and to transfer this information to the control unit 30. The information of the medical equipment 40.n also meets here. These data are then represented together or alone via the spatial display unit 20. Both the three-dimensional operation area and status data of the medical equipment 40.n can be displayed here. The touch-sensitive display overlay 25 makes it possible for the surgeon to input control commands and thus either to select views of the operation area (multi-window technique, PIP, etc.), to call up status data or their progress or also to control the medical equipment.

The invention relates to a visual device for the spatial representation of the operation area during medical operations—preferably during operations on the eye using lasers in order to correct vision defects.

With the invention described here, it is possible to make the operation area visible on a display and to represent it spatially. The invention makes it possible to represent the operation area independently of an operation microscope for a large number of observers. The operation area can be represented much larger, any areas can be magnified or represented simultaneously as a PIP (picture in picture).

In addition to the more natural representation of the operation area, at the same time as the operation, information can be faded in or represented which is important to the doctor and the process of the operation and thus allows complete control of the item of equipment without losing sight of the operation area.

The additional integration of a touch-sensitive display therefore allows complete process control, control of the item of equipment etc. to take place simultaneously.

The present invention therefore represents a solution which makes it possible, during an operation, to represent the operation area spatially on a display for several persons, to fade in any information into the operation area and to control the item of operation equipment—preferably a laser for refractive corneal surgery.

What is claimed is:

1. A device for the three-dimensional representation of an operation area during a laser operation, comprising:
   a spatial recording system;
   an image-processing system;
   a spatial display unit wherein the spatial display includes at least one of a 3-D display, a hologram, and a three-dimensional representation unit generated by a laser; and
   a simulation unit programmed to realize on the display unit a simulated ablation of an eye from at least one laser firing which is yet to occur.

2. The device as recited in claim 1, further comprising:
a control module;
at least one item of medical equipment;
a bus system connecting the spatial display unit and the control module, so that data and information can be displayed on the spatial display unit.

3. The device as recited in claim 1, further comprising a touch-sensitive display overlay.

4. The device as recited in claim 1, wherein the spatial display unit is configured to display image data of the operation area together and a plurality of control panels.

5. The device as recited in claim 4, wherein the spatial display unit is configured to display additional data and information.

6. The device as recited in claim 1, wherein the spatial display unit is configured to display reference data of an ideal operation area after the laser operation simultaneously with an image of the operation area during the laser operation.

7. The device as recited in claim 6, wherein the spatial display unit includes a display of an ideal cornea shape after the laser operation simultaneously with an image of the cornea during the laser operation.

8. The device as recited in claim 1 wherein coordinates for the realization of the simulated ablation are measured by the simulation unit directly from at least one scanner.

9. A method for the three-dimensional representation of an operation area during a laser operation, comprising the steps:
recording the operation area using a spatial recording system;
transferring information obtained from the recording to an image-processing system;
processing the information in an image-processing system; and
representing the processed information three-dimensionally on a spatial display unit;
realizing on the display unit a simulated ablation of an eye from at least one laser firing which is yet to occur.

10. The method as recited in claim 9, further comprising:
representing additional data on the spatial display unit.

11. The method as recited in claim 9, further comprising:
registering a control command; and
controlling a medical equipment device in accordance with the registered control command.

12. The method as recited in claim 11, wherein the registering is performed using a touch-sensitive display on the spatial display unit.

13. A device for the three-dimensional representation of an operation area during a laser operation, comprising:
a spatial recording system;
an image-processing system;
a spatial display unit; and
a simulation unit configured to simulate on the display unit, for each laser firing, a volume removal, wherein the coordinates for the volume removal are measured directly from the scanner on the display.

14. A device for the three-dimensional representation of an operation area during a laser operation of a cornea, the device comprising:
a spatial recording system;
an image-processing system;
a spatial display unit; and
a simulation unit configured to realize on the display unit, for each laser firing, a simulated ablation that simulates a location and a volume ablation of an actual ablation resulting from the laser firing.

15. The device as recited in claim 14, wherein the simulation unit is connected to the control unit.

* * * * *